United States Patent [19]

Swearingen et al.

[11] Patent Number: 4,701,530

[45] Date of Patent: Oct. 20, 1987

[54] TWO-STAGE PROCESS FOR MAKING TRIMETHYL PYRIDINE

[75] Inventors: Loren L. Swearingen, Irving; Randy J. LaTulip, Lake Jackson, both of Tex.

[73] Assignee: The Dow Chemical Company, Midland, Mich.

[21] Appl. No.: 914,203

[22] Filed: Oct. 1, 1986

Related U.S. Application Data

[63] Continuation-in-part of Ser. No. 797,278, Nov. 12, 1985, abandoned.

[51] Int. Cl.⁴ .......................................... C07D 213/09
[52] U.S. Cl. .................................. 546/251; 546/250; 546/349
[58] Field of Search ....................... 546/251, 250, 349

[56] References Cited

U.S. PATENT DOCUMENTS

| | | | |
|---|---|---|---|
| 4,163,854 | 8/1979 | Beschke et al. | 546/251 |
| 4,179,576 | 12/1979 | Miyake et al. | 546/251 |
| 4,482,717 | 11/1984 | Dinkel et al. | 546/251 |

*Primary Examiner*—Alan L. Rotman
*Attorney, Agent, or Firm*—B. G. Colley

[57] ABSTRACT

Process for the production of 2,4,6-trimethyl pyridine wherein a carbonyl compound such as acetone is reacted with ammonia in the presence of a condensation catalyst at a temperature in the range from 100° to 200° C. to produce a mixture of products containing 2,2,4,6-tetramethyl-1,2-dihydropyridine which is then purified. The substantially pure dihydropyridine is then contacted with a cracking catalyst at a temperature in the range from 250° to 450° C. to produce 2,4,6-trimethyl pyridine in high yield.

6 Claims, No Drawings

TWO-STAGE PROCESS FOR MAKING TRIMETHYL PYRIDINE

CROSS REFERENCE TO RELATED APPLICATIONS

This application is a continuation-in-part of Ser. No. 797,278 filed Nov. 12, 1985, abandoned.

BACKGROUND OF THE INVENTION

The invention is a process for the production of 2,4,6-trimethyl pyridine wherein a carbonyl compound is reacted with ammonia to form a mixture containing 2,2,4,6-tetramethyl-1,2-dihydropyridine, the mixture is purified and the purified mixture is converted to 2,4,6-trimethyl pyridine in high yields.

Technical grade collidine or 2,4,6-trimethyl pyridine (TMP) is commercially available as a coal tar extract and contains a mixture of trimethyl and dimethyl pyridines which are difficult to separate due to their close boiling points.

There are many known synthetic methods to make 2,4,6-trimethyl pyridine as is illustrated by U.S. Pat. Nos. 3,781,292; 3,829,429 and 4,140,690.

It is known from U.S. Pat. No. 2,796,421 to react ketones and ammonia over a catalyst to make trimethyl pyridines. However, these single pass processes give low yields as is shown by the controls set forth herein.

SUMMARY OF THE INVENTION

It has now been discovered that 2,4,6-trimethyl pyridine can be made in high yields and high purity by a process wherein a carbonyl compound such as acetone can be reacted with ammonia at a relatively low temperature to make a crude mixture of products containing 2,2,4,6-tetramethyl-1,2-dihydropyridine (tetrapyre) which is then purified and converted over a catalyst at a high temperature into 2,4,6-trimethyl pyridine (TMP).

The essential steps in the process of this invention are:
(A) reacting a carbonyl compound with ammonia in the presence of a condensation catalyst at a temperature in the range from about 100° to about 200° C. and using a suitable mole ratio of reactants, pressure range, and space velocity range to form a mixture containing a high 2,2,4,6-tetramethyl-1,2-dihydropyridine content;
(B) recovering said dihydropyridine in a substantially purified form;
(C) contacting said purified dihydropyridine with a cracking catalyst in the presence of a molar excess of a gaseous diluent at a temperature in the range from about 250° to about 450° C., and with a suitable space velocity and pressure range to prepare a mixture containing a high TMP content; and
(D) recovering TMP from said mixture.

DETAILED DESCRIPTION OF THE INVENTION

The process of this invention in the first step, reacts a carbonyl compound with ammonia. While acetone is the preferred starting material, other compounds such as mesityl oxide and diacetone alcohol can be utilized.

The first step is carried out with an ammonia to carbonyl compounds mole ratio in the range 0.5:1 to 20:1 with the preferred range being 2:1 to 6:1. Higher mole ratios give no advantage while lower mole ratios lead to decreased yields of 2,2,4,6-tetramethyl-1,2-dihydropyridine (tetrapyre).

The temperature should be in the range from 100° to 200° C. and the preferred range is 120° to 150° C.

The liquid hourly space velocity of the reactants through the catalyst should be in the range 0.05 to 1.0 reciprocal hours and preferably in the range 0.1 to 0.5.

The pressure range should be in the range from 25 to 500 pounds per square inch and preferably 40 to 100 psi.

The catalyst necessarily employed in carrying out the initial step of the invention comprises one or more of the compounds generally termed condensation catalysts. These compounds can be either acidic or basic and may be organic or inorganic in composition. Examples of appropriate acidic condensation catalysts include: HCl, HBr, $CH_3COOH$, $H_3PO_4$, $H_2SO_4$, oxalic acid, silica, activated alumina, silica alumina, activated bauxite, $ZnCl_2$, $NH_4Cl$, $CaCl_2$, $FeCl_3$ and $HNO_3$. Examples of appropriate basic condensation catalysts include; sodium hydroxide, calcium hydroxide, lithium hydroxide, potassium hydroxide, magnesium hydroxide, magnesium oxide, calcium oxide, lithium carbonate, sodium carbonate, potassium carbonate, sodium-cesium zeolite, and potassium oxide.

The reaction product of the first reaction is recovered and purified. The light products i.e. acetone, ammonia, acetone imine, mesityl oxide and mesityl imine can be flashed off and recycled to the reactor. The remainder can be distilled preferably under a nitrogen atmosphere and under a pressure in the range from 5 psi to 150 psi and a temperature range from 60° C. to 180° C. The overhead fraction is a water-tetrapyre azeotrope which can be phase separated to recover the tetrapyre.

The demethylation of tetrapyre is carried out at a temperature range from 250° to 450° C. and preferably in the range from 300° to 350° C. with an inert gaseous diluent or atmosphere such as ammonia, nitrogen, or mixture of ammonia and nitrogen.

The gaseous diluent to tetrapyre feed ratios should be in the mole ratio range of 0.2:1 to 10:1 and preferably in the range 1:1 to 4:1.

The liquid hourly space velocity should be in the range 0.05 to 4.0 and preferably 0.25 to 1.0 reciprocal hours.

The pressure range for the demethylation step should be in the range from 5 to 500 pounds per square inch and preferably in the range 10 to 100 psi.

Catalysts which are useful in the demethylation step are generally termed cracking catalysts. These catalysts are based on activated alumina, silica-alumina or an activated zeolite compositon. Enhanced demethylation activity has been observed when employing a dehydrogenation metal or metal compound along with these "cracking catalysts". Example of metals possessing relatively high dehydrogenation activities or properties include: chromimum, nickel, iron, cobalt, manganese, vanadium, titanium scandium, copper, zinc molybdenum, rubidium, platinum, palladium, rhodium, rhenium, tungsten, silver, and cadmum. These metals may be employed individually or in the form of mixtures or alloys thereof, such alloys or mixtures comprising, for example: silver and copper, nickel and molybdenum; and nickel and tungsten.

Still another group of dehydrogenating compounds comprises the oxides, halides, sulfides, selenides, tellurides, molybdates, chromates, bichromates, manganates, of the above class of metals.

Any one or a plurality of the above metal or metal compounds possessing dehydrogenating activity may be used in admixture with the cracking catalysts or as a deposit on the surface of the cracking substrates. These compound catalysts may be prepared in a variety of suitable manners, a convenient method comprising the impregnation of the activated alumina or zeolite with a solution of a metal or metal compound. In any case, anyone skilled in the art may readily prepare a catalyst of any desired initial or final composition. These catalysts may be employed in a suitable form as for example in the form of pellets, granules, or powders of any desired size.

The 2,4,6-trimethyl pyridine can be recovered from the demethylated product by distillation at a temperature in the range from 75° C. to 280° C. and a pressure in the range from 5 psi to 10 psi.

The following examples and controls are presented to further illustrate but not limit the invention set forth in the claims.

EXAMPLES 1-4

Tetrapyre(2,2,4,6-tetramethyl-1,2-dihydropyridine) Production

A series of runs were made in an electrically heated 316 stainless steel reactor having a diameter of 2.5 inches with an effective catalyst depth of 18.5 inches. The catalyst was a nickel/molydenum on alumina product supplied as $\frac{1}{8}''$ extrusions and contained 27.0% $MoO_3$ and 6.7% NiO. Acetone and ammonia were fed into the top of the reactor via separate lines of ammonia to acetone mole ratio that varied for each example. The liquid hourly space velocity (LHSV) ranged from 0.07 to 0.50 hr$^{-1}$. The reactor was pressure controlled from 40 to 90 psig. Reactor temperatures ranged from 90° to 160° C. and were controlled to maintain isothermal conditions. The product exiting the reactor was condensed in a stainless steel heat exchanger and sampled for analysis by gas chromatography. The results from these runs are summarized in Table I. Control 1 illustrates the low yields obtained by using a lower temperature.

TABLE 1

Ni/Mo on Alumina Catalyst Steady State Data

| Run | Example 1 | Example 2 | Example 3 | Example 4 | Control 1 |
|---|---|---|---|---|---|
| LHSV, hr$^{-1}$ | 0.07 | .25 | 0.5 | 0.25 | 0.5 |
| Temperature, °C. | 130 | 130 | 136 | 151 | 95 |
| Pressure, psig | 40 | 40 | 70 | 70 | 70 |
| NH$_3$/Acetone Mole Ratio | 4 | 4 | 1.5 | 4 | 2.5 |
| Product Composition wt % (dry basis) | | | | | |
| Light products | 0.3 | 0.1 | 0.1 | <0.1 | 0.1 |
| Acetone | 63.4 | 91.9 | 92.9 | 82.4 | 78.5 |
| Acetone Imine | 0.8 | 0.4 | 0.4 | 1.0 | 0.1 |
| Mesityl Oxide | 0.6 | 0.9 | .1.8 | 1.6 | 2.2 |
| Tetrapyre* | 30.5 | 4.9 | 4.2 | 10.4 | 1.5 |
| Acetonin** | 1.0 | 1.3 | 0.4 | 1.7 | 7.8 |
| Phorone | 0.6 | 0.2 | — | 0.2 | <0.1 |
| Isophorone | 0.2 | <0.1 | <0.1 | 0.3 | 2.0 |
| Heavy Products | 2.6 | 0.3 | 0.1 | 2.2 | 5.7 |
| Acetone conv. by wt. | 41.9 | 9.9 | 8.7 | 21.0 | 25.5 |
| Tetrapyre yield | 84.7 | 61.6 | 60.3 | 60.2 | 7.1 |

*2,2,4,6-tetramethyl-1,2-dihydropyridine
**2,2,4,6,6-pentamethyltetrahydropyrimidine

EXAMPLES 5-9

Several acidic and basic solid catalysts were evaluated for their utility in the preparation of tetrapyre from acetone and ammonia. A one inch (internal diameter) stainless steel reactor was employed, though the process scheme remained consistent with that described in Examples 1-4. The effective catalyst depth was approximately 19 inches in each experiment and all catalysts were $\frac{1}{8}''$ extrudates. The study was conducted under conditions similar to those described in Examples 1-4. A summary of the results is presented in Table II.

TABLE II

TETRAPYRE PRODUCTION

| | Silica/Alumina* Example 5 | Silica/Alumina* Example 6 | MgO-1 Ex. 7 | MgO-2 Ex. 8 | Zeolite Ex. 9 |
|---|---|---|---|---|---|
| LHSV, hr$^{-1}$ | 0.5 | 0.5 | 0.5 | 0.5 | 0.5 |
| Temperature, °C. | 110 | 194 | 120 | 144 | 175 |
| Pressure, psig | 40 | 40 | 70 | 65 | 100 |
| NH$_3$/Acetone Mole Ratio | 1.9 | 1.9 | 2.2 | 1.6 | 3.7 |
| Product Composition wt % (dry basis) | | | | | |
| Light Products | <0.1 | <0.1 | 0.8 | 0.5 | 0.3 |
| Acetone | 93.0 | 84.8 | 85.3 | 83.8 | 82.4 |
| Acetone Imine | 0.2 | 0.2 | 0.1 | <1.0 | 1.8 |
| Mesityl Oxide | 2.9 | 4.4 | 0.9 | 1.1 | 2.9 |
| Tetrapyre | 3.4 | 6.4 | 11.6 | 12.7 | 8.8 |
| Acetonin | 0.4 | 1.5 | 0.7 | 0.5 | 0.7 |
| Phorone | <0.1 | <0.1 | 0.3 | <0.1 | 0.1 |
| Isophorone | <0.1 | 0.8 | 0.3 | 0.6 | 2.4 |
| Heavy Products | 0.2 | 1.9 | <0.1 | 0.7 | 0.6 |
| Acetone Conversion by Wt. | 8.6 | 18.3 | 17.7 | 19.4 | 21.1 |
| Tetrapyre yield, % | 49.3 | 42.8 | 80.3 | 79.9 | 50.7 |

*Silica/Alumina = Girdler silica alumina T-869
MgO-1 = MgO base catalyst - 30% by weight Avery clay
MgO-2 = MgO base catalyst - 4% Methocel**
Zeolite = Cs,Na Zeolite
**a trademark of THE DOW CHEMICAL COMPANY

EXAMPLE 10

The reaction product from Example 1 was distilled using a five-tray Oldershaw column to obtain a high purity tetrapyre fraction. Approximately 600 grams of the crude product was charged to a 1000 cc distillation flask. The remaining distillation hardware consisted of overheads condenser, product receiver; vacuum pump, and electric flask mantle for heating. An initial lights fraction was recovered at 55° C. and atmospheric pressure. The composition of the light fraction was 64 wt % acetone, 32 wt % water, and 3 wt % dissolved NH$_3$ with minor amounts of low boiling organics. The recovered lights fraction made up approximately 52% (by weight) of the initial charged reaction product. A second, H$_2$O/tetrapyre, fraction was obtained at a 95° C. overhead temperature and atmospheric pressure. The 70/30 (wt/wt) H$_2$O/tetrapyre azeotrope was phase separated and the tetrapyre added back to the distillation flask. The recovered water fraction was approximately 10% (by weight) of the original charge. A third, tetrapyre, fraction was then obtained at a 65° C. overhead temperature and 10 mm Hg vacuum. The tetrapyre fraction accounted for approximately 15% (by weight) of the initial charge.

The weight % composition of the tetrapyre fraction is presented in Table III. An additional 15 wt % of the reaction charge was recovered as ammonia vapor in the initial fraction.

TABLE III

| Tetrapyre Fraction | | | |
|---|---|---|---|
| | Wt % | | Wt % |
| Tetrapyre | 92.1 | Mesityl oxide | 1.1 |
| Diacetone Alcohol | 2.8 | Phorone | 2.0 |
| Heavies | 2.0 | | |

EXAMPLES 11–13

(Tetrapyre Demethylation)

The tetrapyre fraction of Example 10 was fed to a one inch (internal diameter) stainless steel reactor having an effective catalyst height of 19 inches. A commercial Ni/Mo on alumina catalyst was employed for the experiment. The catalyst consisted of 6.7 weight percent nickel oxide and 27.0 weight percent molydenum oxide and the remainder was alumina. The tetrapyre demethylation was completed at a 0.25 hr$^{-1}$ LHSV, 40 psig, 340° C., and a 4/1 feed gas to liquid feed mole ratio. Three separate runs were made at three distinct feed gas compositions: 100% $N_2$, 50/50 (mol/mol) $N_2/NH_3$, and 100% $NH_3$. A summary of the results is presented in Table IV.

TABLE IV

| | 2,4,6-Trimethyl Pyridine Production | | |
|---|---|---|---|
| Product Wt % (dry basis) | Example 11 | Example 12 | Example 13 |
| Lights | 0.5 | 0.5 | 1.1 |
| Acetone | 1.2 | 1.4 | 1.2 |
| Acetone Imine | 0.1 | 0.2 | <0.1 |
| Mesityl Oxide | 0.1 | <0.1 | <0.1 |
| Picoline | <0.1 | 1.2 | 1.3 |
| Mesitylene | 29.0 | 21.2 | 16.4 |
| Tetrapyre | 1.8 | 1.1 | 3.6 |
| Acetonin | 0.4 | 0.2 | 0.1 |
| Diacetone Alcohol | 0.2 | 0.2 | 0.5 |
| 2,4,6-Trimethyl Pyridine (TMP) | 61.8 | 68.3 | 71.1 |
| Phorone | 0.4 | 0.7 | 0.7 |
| Isophorone | 0.6 | 0.6 | 0.4 |
| Heavies | 3.9 | 4.4 | 3.6 |
| Tetrapyre Conversion (wt %) | 98.4 | 99.0 | 96.8 |
| TMP Yield (%) | 63.2 | 68.3 | 71.2 |

An overall yield to TMP of 60% is observed from acetone and ammonia using this two-step process.

CONTROL 2

Employing the same catalyst as described in Example 1 and the same reaction scheme described in Examples 5–9, a single-pass acetone and ammonia experiment was performed. The reactor conditions under which the experiment was completed were: 40 psig, 355° C., 0.25 hr$^{-1}$ LHSV, and a 4/1 ammonia to acetone mole ratio. The experimental results are presented in Table V.

TABLE V

| Single-Pass Acetone/Ammonia Experiment | |
|---|---|
| Product Weight % (dry basis) | |
| Light Products | 3.7 |
| Acetone | 14.6 |
| Acetone Imine | 2.0 |
| Mesityl Oxide | 1.4 |
| Picoline | 7.2 |
| Mesitylene | 2.0 |
| Tetrapyre | 10.9 |
| Acetonin | 1.7 |
| 2,4,6-Trimethyl Pyridine (TMP) | 32.5 |
| Phorone | 0.5 |
| Isophorone | 0.1 |
| Heavy Products | 23.4 |

TABLE V-continued

| Single-Pass Acetone/Ammonia Experiment | |
|---|---|
| Product Weight % (dry basis) | |
| Acetone Conversion, wt % | 87.2 |
| TMP Yield, % | 47.1 |

CONTROLS 3–6

Employing the same reactor scheme as described in Examples 5–9, single-pass acetone and ammonia experiments were performed in the presence of several different solid catalysts. A summary of the acetone conversions and 2,4,6-trimethyl pyridine yields obtained in these experiments is presented in Table VI.

TABLE VI

| | Single-Pass Acetone/Ammonia Experiments | | | |
|---|---|---|---|---|
| CATALYST* | Control 3 Pd/Alumina | Control 4 Pt—Re/ Alumina | Control 5 MgO | Control 6 Zeolite |
| LHSV, hr$^{-1}$ | 0.5 | 0.5 | 0.5 | 0.5 |
| Temperature, °C. | 399 | 399 | 417 | 422 |
| Pressure, psig | 10 | 10 | 70 | 70 |
| $NH_3$/Acetone Mole Ratio | 0.4 | 0.4 | 2.1 | 3.7 |
| Acetone Conversion, % by wt | 97.0 | 82.7 | 21.5 | 36.2 |
| TMP Yield, % | 13.6 | 21.0 | 3.3 | 7.5 |

*Pd/Alumina = 0.3% palladium as oxide on alumina
Pt—Re/Alumina = 0.5% platinum-rhenium on alumina
MgO = magnesium oxide - 4% METHOCEL**
Zeolite = Cs, Na zeolite
**a trademark of THE DOW CHEMICAL COMPANY

What is claimed is:

1. A method for the preparation of 2,4,6-trimethyl pyridine (TMP) in high yields which comprises
    (A) reacting a carbonyl compound with ammonia in the presence of a condensation catalyst at a temperature in the range from about 100° to about 200° C. and using a suitable mole ratio of reactants, pressure range, and space velocity range to form a mixture containing a high 2,2,4,6-tetramethyl-1,2-dihydropyridine content;
    (B) recovering said dihydropyridine in a substantially purified form;
    (C) contacting said purified dihydropyridine with a cracking catalyst in the presence of a molar excess of a gaseous diluent at a temperature in the range from about 250° to about 450° C., and with a suitable space velocity and pressure range to prepare a mixture containing a high TMP content; and
    (D) recovering TMP from said mixture.
2. The method of claim 1 wherein said gaseous diluent is nitrogen, ammonia or mixtures thereof.
3. The method of claim 1 wherein in step (A) the mole ratio of ammonia to carbonyl compound is in the range from 0.5:1 to 20:1; the pressure range is from 25 to 500 psig; and the liquid hourly space velocity range is from 0.05 to 1.0 reciprocal hours.
4. The method of claim 1 wherein in step (C) the molar excess of diluent to dihydropyridine is in the range from 2:1 to 6:1; the pressure range is from 5 to 500 psig; and the space velocity range is from 0.05 to 4.0 reciprocal hours.
5. The method of claim 1 wherein step B is carried out by distillation at a temperature in the range from 60° C. to 180° C. and a pressure in the range from 5 psi to 10 psi.
6. The method in claim 1 wherein Step C is carried out in the presence of alumina or silica alumina catalysts containing nickel-molybdenum oxides or nickel-tungsten oxides.

* * * * *